United States Patent
Grifols Lucas

(10) Patent No.: US 6,832,463 B2
(45) Date of Patent: Dec. 21, 2004

(54) METHOD FOR THE STERILE DOSING OF VIALS

(75) Inventor: Victor Grifols Lucas, Parets del Valles (ES)

(73) Assignee: Probitas Pharma S.A., Barcelona (ES)

(*) Notice: Subject to any disclaimer, the term of this patent is extended or adjusted under 35 U.S.C. 154(b) by 0 days.

(21) Appl. No.: 10/755,973

(22) Filed: Jan. 12, 2004

(65) Prior Publication Data

US 2004/0139698 A1 Jul. 22, 2004

(30) Foreign Application Priority Data

Jan. 21, 2003 (ES) .......................................... 200300143

(51) Int. Cl.$^7$ .............................................. B65B 55/04
(52) U.S. Cl. ............................ 53/426; 53/425; 53/167
(58) Field of Search .......................... 53/425, 426, 167; 134/22.1; 422/26, 302

(56) References Cited

U.S. PATENT DOCUMENTS

| | | | |
|---|---|---|---|
| 4,230,231 A | * | 10/1980 | Burnett et al. .............. 215/329 |
| 4,969,915 A | * | 11/1990 | Hatanaka et al. ............. 53/425 |
| 5,609,819 A | * | 3/1997 | Shimizu et al. ................ 422/3 |
| 5,673,535 A | * | 10/1997 | Jagger .......................... 53/282 |
| 6,189,292 B1 | * | 2/2001 | Odell et al. ................... 53/425 |
| 6,199,350 B1 | * | 3/2001 | Brechel et al. ............... 53/510 |
| 6,494,865 B1 | * | 12/2002 | Alchas ........................ 604/192 |

FOREIGN PATENT DOCUMENTS

ES          2 016 490          11/1990

* cited by examiner

Primary Examiner—Eugene Kim
Assistant Examiner—Hermant M Desai
(74) Attorney, Agent, or Firm—Darby & Darby

(57) ABSTRACT

A method for sterile dosing of vials comprises a step for fitting stopper and cap assemblies together and washing vials. The stopper/cap assembly is then fitted with its external protector and a step of sterilization in an autoclave under vacuum is then performed. A subsequent step of cooling in laminar airflow to prevent the entry of air and dosing and plugging are then performed with continuous display of the operation and taking of views with a video camera. Followed by encapsulation and re-plugging, step of marking of the glass of the vial by means of laser beams to identify time and dosing information is performed.

4 Claims, 5 Drawing Sheets

METHOD FOR THE STERILE DOSING OF VIALS

FIELD OF THE INVENTION

The present invention is intended to disclose a novel method for the dosing of sterile vials which provides notable characteristics of novelty and inventive step.

BACKGROUND OF THE INVENTION

The present invention relates to a method for the dosing of sterile vials which is applicable to medicinal products and is based on the principle disclosed in Patent Spanish 8902737 in the name of Probitas Pharma, S. A., for the preparation and dosing of sterile vials, in order to provide a guarantee of safety in the sterility of the dosing; in that patent, the vial is sterilized with the stopper and the cap fitted, the stopper having a special design so as to be fitted on the top of the vial without plugging it completely so that steam can enter during the sterilization cycle. Moreover, the assembly is protected by a protector which has a dual purpose since, on the one hand, it protects the interior of the vial against possible contamination and, on the other hand, it offers protection against possible accidental plugging of the vial during handling. This method represents a notable improvement in safety since the interior of the vial is exposed minimally to the environmental air and is only opened at the moment when the dosing is performed, the vial being re-plugged with the same stopper; this method also reduces the time of exposure with the vial open and, as a result, minimizes the potential danger of contamination.

SUMMARY OF THE INVENTION

The present invention considerably improves the correct sterile dosing of the vials by disclosing a method in which the following steps are performed in succession a) assembling the stopper with the cap in a specific machine which has supply hoppers for the stoppers and caps that fit the assembly together automatically;

b) washing the vials in a specific machine for that task, in which the cleanliness of the vial is ensured;

c) fitting together the vial, stopper/cap, and protector in a device which is normally coupled to the output of the vial-washing machine and which cleans the interior of the stopper, fits the vial assembly together in the partial closure position, puts the protector in place, and then arranges the vials in trays for the loading of an autoclave;

d) a step of sterilization in the autoclave in which the vials arrive on trays disposed on tray-carrying trolleys, the sterilization being performed with pure steam with a vacuum cycle for complete sterilization of the assembly;

e) a vial-cooling step which is performed on the sterile side of the autoclave, minimizing the risk of air entering as the vial cools by reduction of the air density, this process taking place in a zone with maximum environment control and quality and a low laminar flow of filtered air (Class A);

f) loading the vials with their stoppers, caps, and protectors, into an accumulation turntable for intermediate collection purposes;

g) dosing and plugging in a zone of the dosing machine which is in Class A conditions and is subjected to a laminar flow that is normally horizontal; during this stage, the vial, from which the protector has previously been removed by a manipulator, is introduced with the stopper/cap assembly fitted in the partial closure position in a manner such that a manipulator removes the stopper/cap assembly and supports it whilst the dosing nozzle is positioned above the vial and doses the desired quantity of liquid of the sterile solution. The stopper/cap assembly is then replaced on the same vial, the said assembly being pressed as far as the total closure position, that is, leaving the vial hermetically sealed. During this stage, a video camera is provided and performs continuous recording related to the duration and time determined by the dosing machine.

In the filled state, there is no obstacle between the horizontal laminar flow and the mouth of the vial, which favours the protection of the sterile conditions of the vial;

h) a step of encapsulation under laminar flow with a machine which is connected to the dosing machine and performs the flanging of the cap in order to close it; this machine has, at its output, a system for marking the glass of the vial with laser beams; this identifies each vial and provides information on the time of dosing; together with the video recording, this enables the route followed and any dosing problems to be monitored;

i) discharging the vials into an output turntable of the machine which permits the collection and discharge thereof.

BRIEF DESCRIPTION OF THE DRAWINGS

For a better understanding, some schematic drawings of the present invention are appended by way of non-limiting example.

DETAILED DESCRIPTION OF THE DRAWINGS

Figure 1:
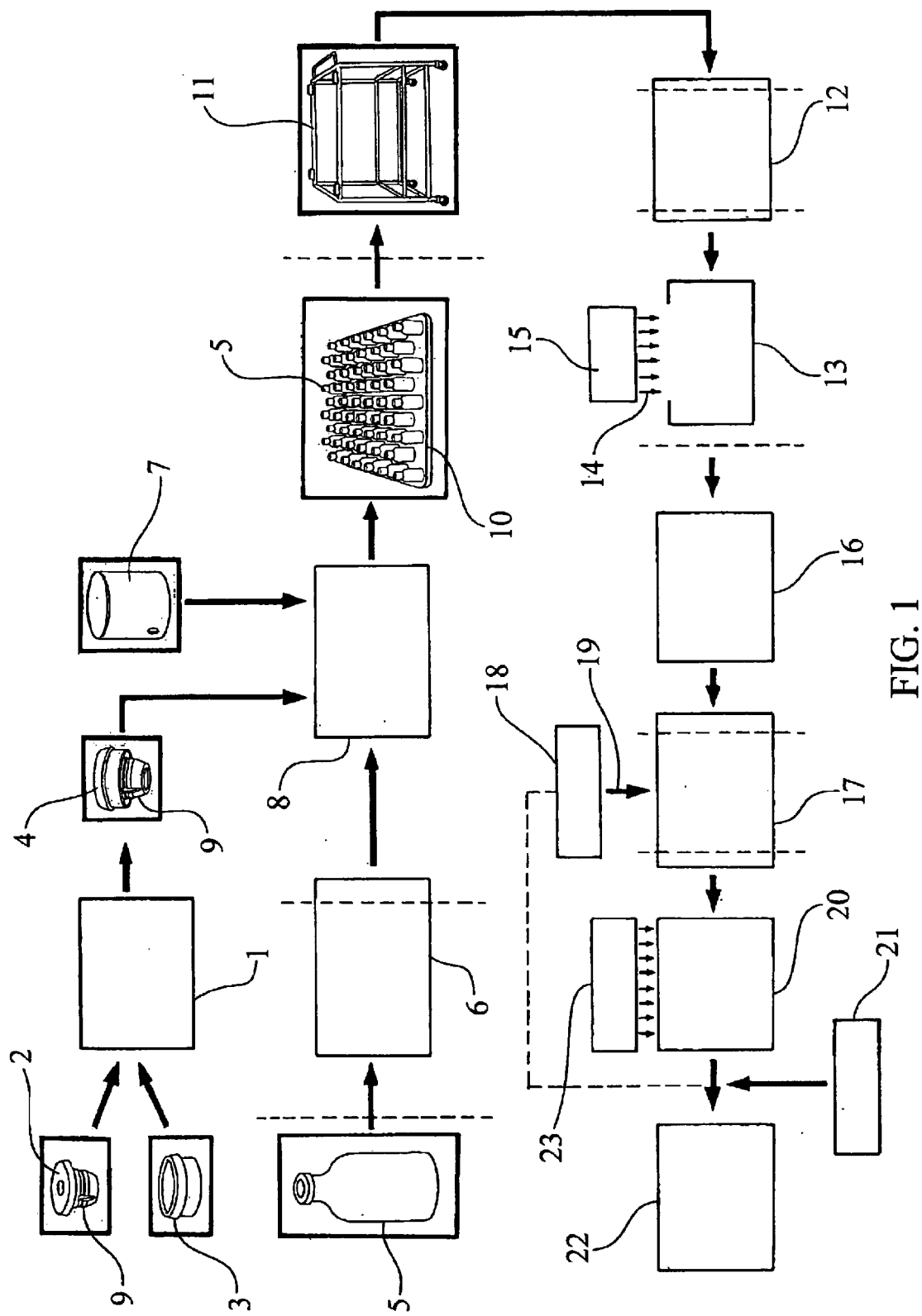
FIG. 1 shows a complete diagram of the operative steps of the method of the present invention.

As can be seen in the schematic drawing which is appended in the form of FIG. 1, the first operative step of the method of the present invention is performed in a machine 1 for fitting a stopper 2 and a cap 3 together, forming an assembly 4. The said machine is based on hoppers for supplying the stopper and the cap and automatically provides the stopper and cap assembly.

The second step of the method relates to the washing of vials 5. It is performed in a vial-washing machine 6 which is intended to ensure complete cleanliness of the vial.

The next step of the method is performed in a machine for fitting the vial with the stopper/cap assembly and a protector 7. This fitting machine, which is indicated 8, receives the clean vials from the machine 6 and the protectors 7, performing the cleaning of the interior of the stopper and fitting the assembly in the vial in the position in which the stopper is not completely closed, permitting the passage of steam and air through an axial groove 9 of the stopper 2. The protector 7 is put in place in the machine 8 itself and the vials 5 with the stopper/cap and the protector are then placed on trays 10 to be loaded into an autoclave. The said trays are incorporated in tray-carrying trolleys which are indicated schematically by way of example by the numeral 11.

The next step takes place in an autoclave 12 in which the assemblies comprising the vial with its stopper/cap and protector, transported by the carriages 11, are sterilized with pure steam.

The next step of the method takes place on the sterile side of the autoclave in a zone indicated 13 and is intended to bring about cooling by means of an air-flow 14 generated by suitable means 15, performing the cooling in aseptic conditions of the type indicated by Class A, acting on the whole load of vials. This cooling step minimizes the risk of air entering the vial as the vial cools since the cooling process takes place in a zone of maximum environment control and quality. It is essential at this stage to produce a laminar flow, indicated by the arrows 14, in which there is a completely unidirectional cooling circuit from the input of the device 15 to the outlet at the lower side which again minimizes the possibilities of contamination.

The vials with their stoppers, caps, and protectors are then loaded into an accumulation turntable, indicated schematically by the numeral 16.

The plugging and dosing takes place in the next step, indicated 17, in which the dosing zone is in Class A conditions with a laminar flow produced by means 18 and indicated by the arrow 19. In this step, the vial, from which the protector has previously been removed by a manipulator, is introduced, with the stopper/cap mounted in the partial or pre-plugging position; another manipulator removes the stopper/cap assembly, holding it in the removed position whilst the dosing nozzle is positioned above the vial and doses the quantity of liquid of the sterile solution. The stopper/cap assembly is then refitted on the same vial, closing the assembly completely, that is, leaving the vial completely closed hermetically. This step is complemented by video monitoring which provides for continuous recording related to the duration and time determined by the dosing machine. Moreover, the dosing machine is equipped with safety barriers of a desired type so that, if any person or object crosses the barriers, the machine stops dosing automatically, preventing risks of contamination owing to the presence of the said person or object in the vicinity of the dosing point.

The next, encapsulation step takes place in the machine unit 20 which is connected to the dosing machine and which performs the crimping of the cap 3 in order to bring about its closure. At the output of the machine, there is a laser marking device 21 which produces marks containing information on the dosing time on the glass of each vial, to identify each vial. This information is intended, together with the video recording, for monitoring of the operations performed on the vial and may assist in the investigation of any dosing problems that arise subsequently.

The process is terminated by the output of the completed vials into an output turntable 22 in which they are collected for subsequent dispatch.

The encapsulation step 20 may also be combined with means 23 for generating a laminar flow.

Figure 2:
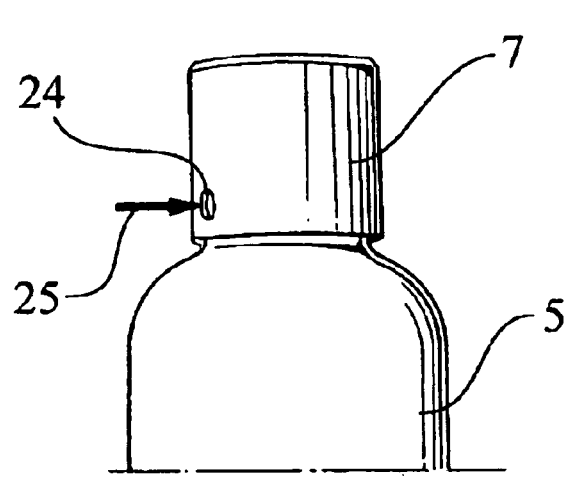
FIGS. 2 to 8 show various details of the stopper and its closure and cap as well as the operations to which it is subjected.
Figure 3:
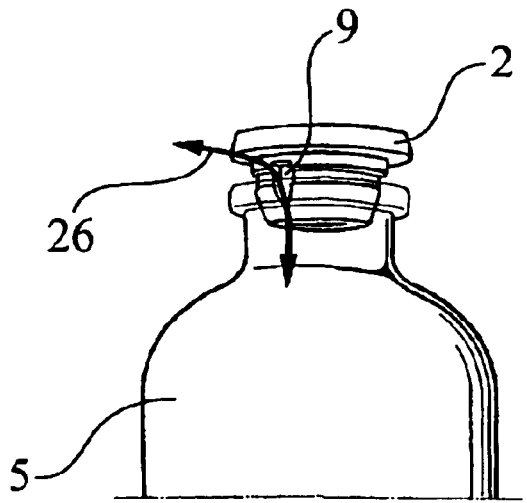

FIGS. 2 to 8 show successive operations on the vial, stopper, and cap, on which the method of the present invention is performed. Thus, for example, FIG. 2 shows the vial 5 provided with the protector 7 which in turn has a hole 24 which can permit the gaseous flow into the vial 5, as shown by the arrows 25 in FIG. 2 and 26 in FIG. 3, in the position in which the stopper 2 is positioned without total closure, since an interchange of gaseous fluids can take place through the groove 9.

Figure 4:
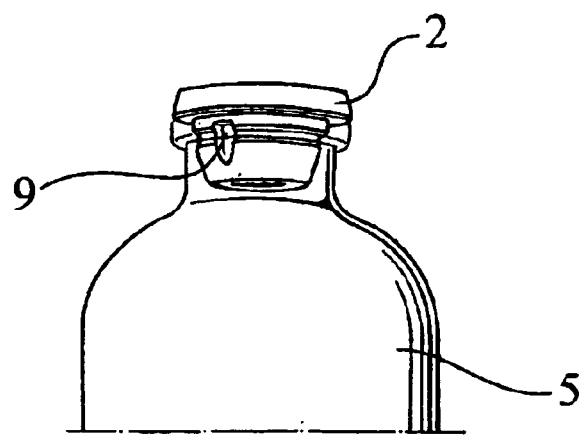
Figure 5:
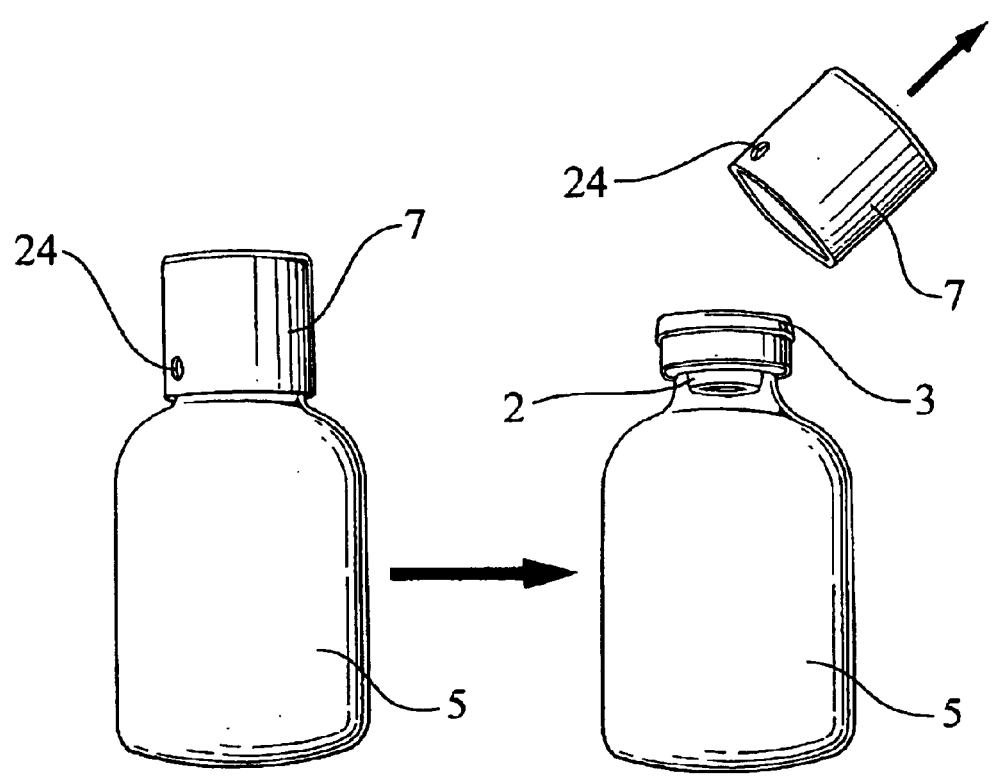
Figure 6:
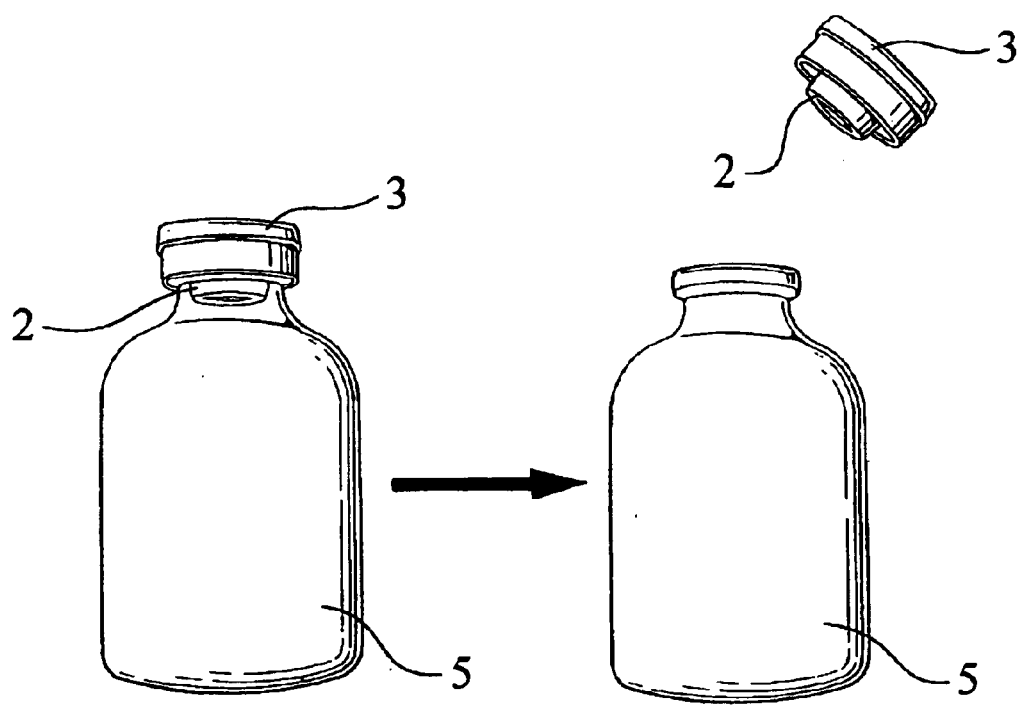
Figure 7:
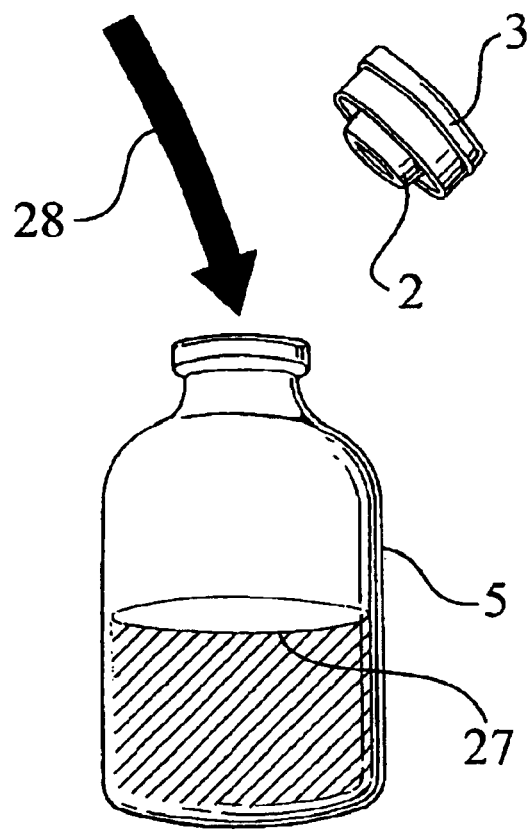
Figure 8:
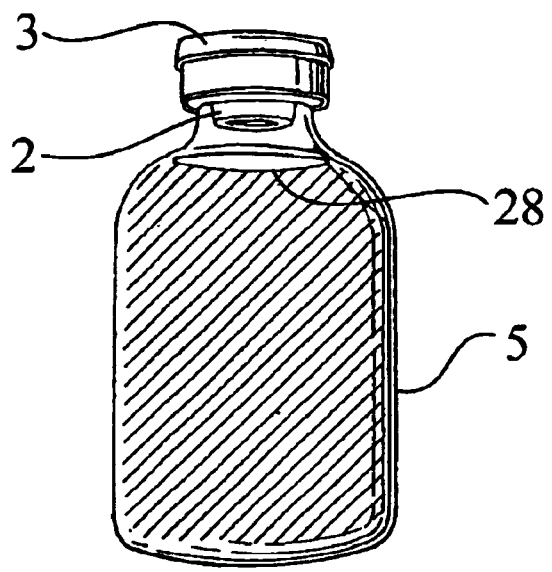

FIG. 4 shows the closed stopper before it receives the cap indicated 3 in FIG. 1, the positioning of which is not shown expressly. In FIG. 5 the step of removing the protector 7 from the neck of the vial 5 can be seen, after which the stopper and cap assembly is removed from the vial as shown in FIG. 6. The dosing is shown in FIG. 7 in which the vial 5 receives the volume 27 of the product which it is intended to contain in a filling step represented by the arrow 28, with the stopper 2 and cap 3 assembly removed. After this step, the repositioning of the stopper and cap assembly, as shown in FIG. 8, with the vial full up to the desired level which is represented in conventional manner by the level line 28, will be completed by the final encapsulation step.

The combination of steps and the means provided for in the present invention will permit easy industrialization of the process, ensuring very high cleanliness and sterility characteristics in the various steps as well as effective rationalization for the purposes of reducing their costs as well as increasing reliability and safety with regard to the sterility of the vials.

What is claimed is:

1. A method for sterile dosing of vials which is characterized by consecutive combination of the following steps:
    a) fitting together assemblies formed by a stopper and its cap for each vial, from supply hoppers for stoppers and caps for fitting the assembly together automatically,
    b) washing of vials in order to clean the vial,
    c) fitting together the assembly formed by the vial, stopper/cap, and external protector, cleaning the interior of the stopper, and fitting the stopper and cap assembly in a partial closure position with communication through a groove of the stopper, putting the protector in place and, finally, placing the vials on trays for the loading of an autoclave,
    d) a step of sterilization in the autoclave with vacuum cycles for complete sterilization of the set of trays carrying the vials with their stopper/cap and protector assemblies on tray-carrying trolleys,
    e) a step of cooling under a laminar flow to reduce the temperature of the vials after the sterilization in the autoclave to prevent the risk of subsequent entry of air into the interior of the vial as a result of the cooling thereof,
    f) a step of loading the cooled vials into a feeding accumulation turntable,
    g) a dosing and plugging step in which the vials, from which the protector has previously been removed by a manipulator, are introduced with the stopper in the partial closure position and a second manipulator removes the stopper and cap assembly, keeping them removed whilst the dosing of the liquid in the form of sterile solution into each vial is performed by means of a specific nozzle, the stopper/cap assembly then being closed completely onto the vial which is hermetically sealed,
    h) a step, simultaneous with step f), for the display and taking of views with a video camera with continuous recording in relation to the duration and time of dosing of the machine,
    i) an encapsulation step with a machine which is connected to the dosing machine of step g) and performs the flanging of the cap in order to close it, and which is combined with a device for marking the glass of the vial by means of laser beams, with identification of the dosing-time information, and
    j) removal of the completed vials into an accumulation turntable.

2. A method for the sterile dosing of vials according to claim 1, characterized in that the cooling of the vials is performed on the sterile side of the autoclave in a unidirectional laminar-flow situation in order to reduce the danger of contamination.

3. A method for the sterile dosing of vials according to claim 1, characterized in that the dosing is performed in Class A conditions with a laminar flow.

4. A method for the sterile dosing of vials according to claim 1, characterized in that the sterilization of the stopper/ cap and vial assembly is performed in a pre-plugging condition in order for plugging in the final position to be performed after dosing.

* * * * *